United States Patent
Lee et al.

(10) Patent No.: US 11,911,188 B2
(45) Date of Patent: Feb. 27, 2024

(54) APPARATUS AND METHOD FOR MONITORING HEALTH, AND MOBILE DEVICE

(71) Applicant: SAMSUNG ELECTRONICS CO., LTD., Suwon-si (KR)

(72) Inventors: So Young Lee, Daejeon (KR); Jeong Eun Hwang, Suwon-si (KR); Ka Ram Choi, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 463 days.

(21) Appl. No.: 16/852,682

(22) Filed: Apr. 20, 2020

(65) Prior Publication Data

US 2021/0128073 A1    May 6, 2021

(30) Foreign Application Priority Data

Oct. 30, 2019  (KR) .......................... 10-2019-0136305

(51) Int. Cl.
   *A61B 5/00* (2006.01)
   *A61B 5/02* (2006.01)
   (Continued)

(52) U.S. Cl.
   CPC ........ *A61B 5/7278* (2013.01); *A61B 5/02007* (2013.01); *A61B 5/0261* (2013.01);
   (Continued)

(58) Field of Classification Search
   CPC .............. A61B 5/7278; A61B 5/02007; A61B 5/02427; A61B 5/0261; A61B 5/0295;
   (Continued)

(56) References Cited

U.S. PATENT DOCUMENTS 8,016,761 B2    9/2011  Friedman et al.
8,313,439 B2   11/2012  McCombie et al.
(Continued)

FOREIGN PATENT DOCUMENTS

EP    1 584 289 A2   10/2005
EP    2 904 968 A1    8/2015
(Continued)

OTHER PUBLICATIONS

NPL Zhang (Aihua, Zhang, et al. "Pulse signals detection by digital image correlation." 2008 International Conference on BioMedical Engineering and Informatics. vol. 2. IEEE, 2008.), (Year: 2008).*

(Continued)

*Primary Examiner* — Alex M Valvis
*Assistant Examiner* — Chanel J Jhin
(74) *Attorney, Agent, or Firm* — Sughrue Mion, PLLC

(57) ABSTRACT

Provided is an apparatus for non-invasively monitoring a health condition. The apparatus for monitoring health according to an example embodiment of the disclosure includes: a pulse wave sensor configured to obtain a first pulse wave signal in a first contact state of an object and a second pulse wave signal in a second contact state of the object; and a processor configured to estimate a degree of vasodilation based on an alternating current (AC) component of each of the first pulse wave signal and the second pulse wave signal, configured to monitor a vascular health condition based on the estimated degree of vasodilation, and configured to output a result of monitoring the vascular health condition.

22 Claims, 12 Drawing Sheets

(51) Int. Cl.
  *A61B 5/024* (2006.01)
  *A61B 5/026* (2006.01)
  *A61B 5/0295* (2006.01)

(52) U.S. Cl.
  CPC ........ *A61B 5/0295* (2013.01); *A61B 5/02427* (2013.01); *A61B 5/6843* (2013.01); *A61B 5/6898* (2013.01); *A61B 5/7203* (2013.01); *A61B 5/742* (2013.01)

(58) Field of Classification Search
  CPC ... A61B 5/6843; A61B 5/6898; A61B 5/7203; A61B 5/742
  USPC .......................................................... 600/479
  See application file for complete search history.

(56) References Cited

U.S. PATENT DOCUMENTS

| | | | |
|---|---|---|---|
| 8,706,464 | B2 | 4/2014 | Shusterman |
| 8,755,857 | B2 | 6/2014 | Melker et al. |
| 8,768,424 | B2 | 7/2014 | Crowe et al. |
| 10,376,161 | B2 | 8/2019 | Tanaka |
| 10,568,527 | B2 | 2/2020 | Yoon et al. |
| 2017/0119307 | A1* | 5/2017 | Shim ................ A61B 5/0022 |
| 2018/0177413 | A1* | 6/2018 | Kwon ............... A61B 5/02141 |
| 2019/0104997 | A1 | 4/2019 | Kang et al. |
| 2019/0110758 | A1 | 4/2019 | Kang et al. |
| 2019/0282179 | A1 | 9/2019 | Newberry |
| 2021/0267550 | A1* | 9/2021 | Mukkamala ............ G06F 3/044 |

FOREIGN PATENT DOCUMENTS

| | | |
|---|---|---|
| EP | 3 469 984 A1 | 4/2019 |
| EP | 3 473 170 A1 | 4/2019 |
| KR | 10-0768586 B1 | 10/2007 |
| KR | 10-2016-0028303 A | 3/2016 |
| KR | 10-2017-0049317 A | 5/2017 |
| KR | 10-2018-0021373 A | 3/2018 |

OTHER PUBLICATIONS

Allen, John, "Photoplethysmography and its application in clinical physiological measurement", Physiological Measurement, vol. 28, Feb. 20, 2007, pp. R1-R39.

Gil, Yeongjoon et al., "Design and Implementation of Real-time Blood Pressure Measuring System using Smartphone", KIISE Transactions on Computing Practices, 2015, vol. 21, No. 3, pp. 192-214.

Gryglewski, R. J. et al., "Superoxide anion is involved in the breakdown of endothelium-derived vascular relaxing factor", Nature, 1986, vol. 320, pp. 454-456.

Tesfamariam, Belay, "Free radicals in diabetic endothelial cell dysfunction", Free Radical Biology and Medicine, Mar. 1994, vol. 16, Issue 3, pp. 383-391.

Celermajer, David S. et al., "Non-invasive detection of endothelial dysfunction in children and adults at risk of atherosclerosis", The Lancet, Nov. 7, 1992, vol. 340, No. 8828, pp. 1111-1115.

Communication dated Feb. 9, 2021, issued by the European Patent Office in counterpart European Application No. 20191028.8.

* cited by examiner

APPARATUS AND METHOD FOR MONITORING HEALTH, AND MOBILE DEVICE

CROSS-REFERENCE TO RELATED APPLICATION(S)

This application claims priority from Korean Patent Application No. 10-2019-0136305, filed on Oct. 30, 2019, in the Korean Intellectual Property Office, the entire disclosure of which is incorporated herein by reference for all purposes.

BACKGROUND

1. Field

One or more example embodiments of the disclosure relate to technology for monitoring health, and more particularly to technology for monitoring the function and/or the condition of blood vessels.

2. Description of the Related Art

It has been known that patients with hypertension, hyperlipidemia, diabetes, heart disease, and obesity may have a decreased vascular endothelial function, and thus may suffer from atherosclerosis due to dysfunction in endothelial-dependent vasodilation.

For diagnosis of the vascular endothelial cell dysfunction, invasive and non-invasive diagnosis methods are generally used. While the invasive diagnosis method provides a relatively accurate diagnosis, it requires a complicated test process and an invasive procedure, such that the invasive diagnosis method is not suitable for use as a screening method for assessment of endothelial function. A flow mediated dilation (FMD) test is a commonly used non-invasive diagnosis method. During the FMD test, the internal diameter and velocity of blood flow through blood vessels should be measured by continuously locating blood vessels at the same position by using an ultrasound, such that measurement techniques of experienced and qualified medical personnel are required. Further, the FMD test has limitations in that test results of several testers may not coincide with each other, and the like.

SUMMARY

According to an aspect of an example embodiment, there is provided an apparatus for monitoring health, the apparatus including: a pulse wave sensor configured to obtain a first pulse wave signal in a first contact state of an object and a second pulse wave signal in a second contact state of the object; and a processor configured to estimate a degree of vasodilation based on an alternating current (AC) component of each of the first pulse wave signal and the second pulse wave signal, configured to monitor a vascular health condition based on the estimated degree of vasodilation, and configured to output a result of monitoring the vascular health condition.

The pulse wave sensor may include a light source configured to emit light onto the object; and a detector configured to detect light reflected or scattered from the object.

Based on a request for monitoring health, the processor may be further configured to: provide information on the first contact state to a user to guide the user to touch the pulse wave sensor with the object at a contact pressure of a first pressure; and provide information on the second contact state to the user to guide the user to increase the contact pressure to a second pressure or higher, and upon satisfaction of a condition, to decrease the contact pressure to the first pressure.

Upon providing the information on the first contact state, in response to the AC component of the first pulse wave signal not being detected, the processor may be further configured to again provide the information on the first contact state to the user.

Upon providing the information on the second contact state, in response to the AC component of the second pulse wave signal being detected, the processor may be further configured to increase a value of the second pressure and provide the information on the second contact state with the second pressure having the increased value.

The apparatus may further include a pressure sensor configured to obtain the contact pressure of the object that comes into contact with the pulse wave sensor, and the processor may be further configured to provide the information on the first contact state and the second contact state based on the contact pressure of the object which is obtained by the pressure sensor.

Each of the first pressure and the second pressure may have at least one of a preset value, and a value determined for the user.

The processor may be further configured to determine the value of the first pressure by providing information to guide the user to touch the pulse wave sensor with the object in a resting state, and determining the value of the first pressure based on whether the AC component of the first pulse wave signal is detected while the object is in contact with the pulse wave sensor in the resting state.

The processor may be further configured to determine the value of the second pressure by providing information to guide the user to increase the contact pressure to a predetermined pressure or greater, and determining the value of the second pressure based on whether the AC component of the second pulse wave signal is detected at the contact pressure increased to the predetermined pressure or greater.

The processor may be further configured to estimate a first blood volume based on an area of a first AC component detected from the first pulse wave signal, estimate a second blood volume based on an area of a second AC component detected from the second pulse wave signal, and estimate the degree of vasodilation based on a difference between the first blood volume and the second blood volume.

The processor may be further configured to: correct the area of the first AC component based on a difference between a contact pressure of the object at a time of obtaining the first pulse wave signal and a first pressure corresponding to the first contact state; and correct the area of the second AC component based on a difference between a contact pressure of the object at a time of obtaining the second pulse wave signal and a second pressure corresponding to the second contact state.

In response to the estimated degree of vasodilation being less than a predetermined threshold, the processor may be further configured to determine an abnormality in a function of a blood vessel.

The apparatus may further include an output interface configured to output the result of monitoring the vascular health condition.

According to an aspect of an example embodiment, there is provided a method of monitoring health, including: obtaining a first pulse wave signal in a first contact state of an object; obtaining a second pulse wave signal in a second contact state of the object; estimating a degree of vasodilation based on an alternating current (AC) component of each of the first pulse wave signal and the second pulse wave signal; monitoring a vascular health condition based on the estimated degree of vasodilation; and output a result of monitoring the vascular health condition.

The method may further include, based on a request for monitoring health: providing information on the first contact state to a user to guide the user to touch a pulse wave sensor with the object with a contact pressure of a first pressure; and providing information on the second contact state to the user to guide the user to increase the contact pressure to a second pressure or higher, and upon satisfaction of a condition, to decrease the contact pressure to the first pressure.

The method may further include, upon providing the information on the first contact state, in response to the AC component of the first pulse wave signal not being detected, again providing the information on the first contact state to the user.

The method may further include, upon providing the information on the second contact state, in response to the AC component of the second pulse wave signal being continuously detected, increasing a value of the second pressure and providing the information on the second contact state with the second pressure having the increased value.

The method may further include obtaining the contact pressure of the object by a pressure sensor, and the providing the information on the first contact state and the second contact state may include providing the information on the first contact state and the second contact state based on the contact pressure of the object obtained by the pressure sensor.

The method may further include: determining a value of the first pressure by providing information to guide the user to touch the pulse wave sensor with the object in a resting state, and determining the value of the first pressure based on whether the AC component of the first pulse wave signal is detected while the object is in contact with the pulse wave sensor in the resting state.

The method may further include: determining a value of the second pressure by providing information to guide the user to increase the contact pressure to a predetermined pressure or greater, and determining the value of the second pressure based on whether the AC component of the second pulse wave signal is detected at the contact pressure increased to the predetermined pressure or greater.

The estimating the degree of vasodilation may include: estimating a first blood volume based on an area of a first AC component detected from the first pulse wave signal; estimating a second blood volume based on an area of a second AC component detected from the second pulse wave signal; and estimating the degree of vasodilation based on the first blood volume and the second blood volume.

The estimating the degree of vasodilation may further include: correcting the area of the first AC component based on a difference between a contact pressure of the object at a time of obtaining the first pulse wave signal and a first pressure corresponding to the first contact state; and correcting the area of the second AC component based on a difference between a the contact pressure of the object at a time of obtaining the second pulse wave signal and a second pressure corresponding to the second contact state.

The monitoring the vascular health condition may include, in response to the estimated degree of vasodilation being less than a predetermined threshold, determining an abnormality in a function of a blood vessel.

The method may further include controlling an output interface to output the result of monitoring the vascular health condition.

According to an aspect of an example embodiment, there is provided a mobile device, including: a main body; a pulse wave sensor mounted in the main body and configured to obtain a first pulse wave signal before an occlusion of a blood vessel in an object and obtain a second pulse wave signal after the occlusion of the blood vessel in the object; a processor mounted in the main body, and configured to extract respective alternating current (AC) components from the first pulse wave signal and the second pulse wave signal, and to monitor a vascular health condition based on the extracted respective AC components; and a display configured to output a result of monitoring the vascular health condition.

The processor may be further configured to provide information to guide a user to touch the pulse wave sensor with the object at a contact pressure of a first pressure, upon which the first pulse wave signal is obtained; and the processor may be further configured to provide information to guide the user to increase the contact pressure to a second pressure or higher, and upon satisfaction of a condition, to decrease the contact pressure to the first pressure.

The processor may be further configured to estimate a degree of vasodilation based on an area of an AC component of the first pulse wave signal and an area of an AC component of the second pulse wave signal, and monitor the vascular health condition based on the estimated degree of vasodilation.

In response to the estimated degree of vasodilation being less than a predetermined threshold, the processor may be further configured to determine an abnormality in a function of the blood vessel, and control the display to display a result of determining the abnormality.

The mobile device may further include a communication interface configured to communicate with an external device, and in response to the estimated degree of vasodilation being less than a predetermined threshold, the processor may be further configured to determine an abnormality in a function of the blood vessel, and the communication interface may be further configured to transmit information related to the vascular health condition to the external device.

BRIEF DESCRIPTION OF THE DRAWINGS

The above and other aspects and features of the disclosure will become more apparent by describing in detail example embodiments thereof with reference to the attached drawings.

DETAILED DESCRIPTION

Figure 1:
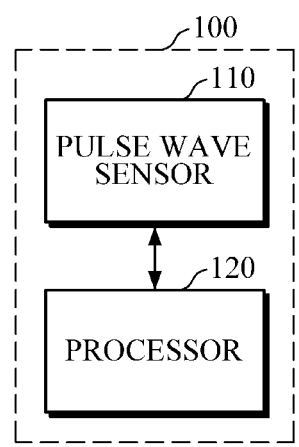
FIG. 1 is a block diagram illustrating an apparatus for monitoring health according to an example embodiment of the disclosure.

Details of example embodiments are included in the following detailed description and drawings. Advantages and features of the disclosure, and a method of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit for processing at least one function or operation and that may be embodied as hardware, software, or a combination thereof.

Figure 2A:
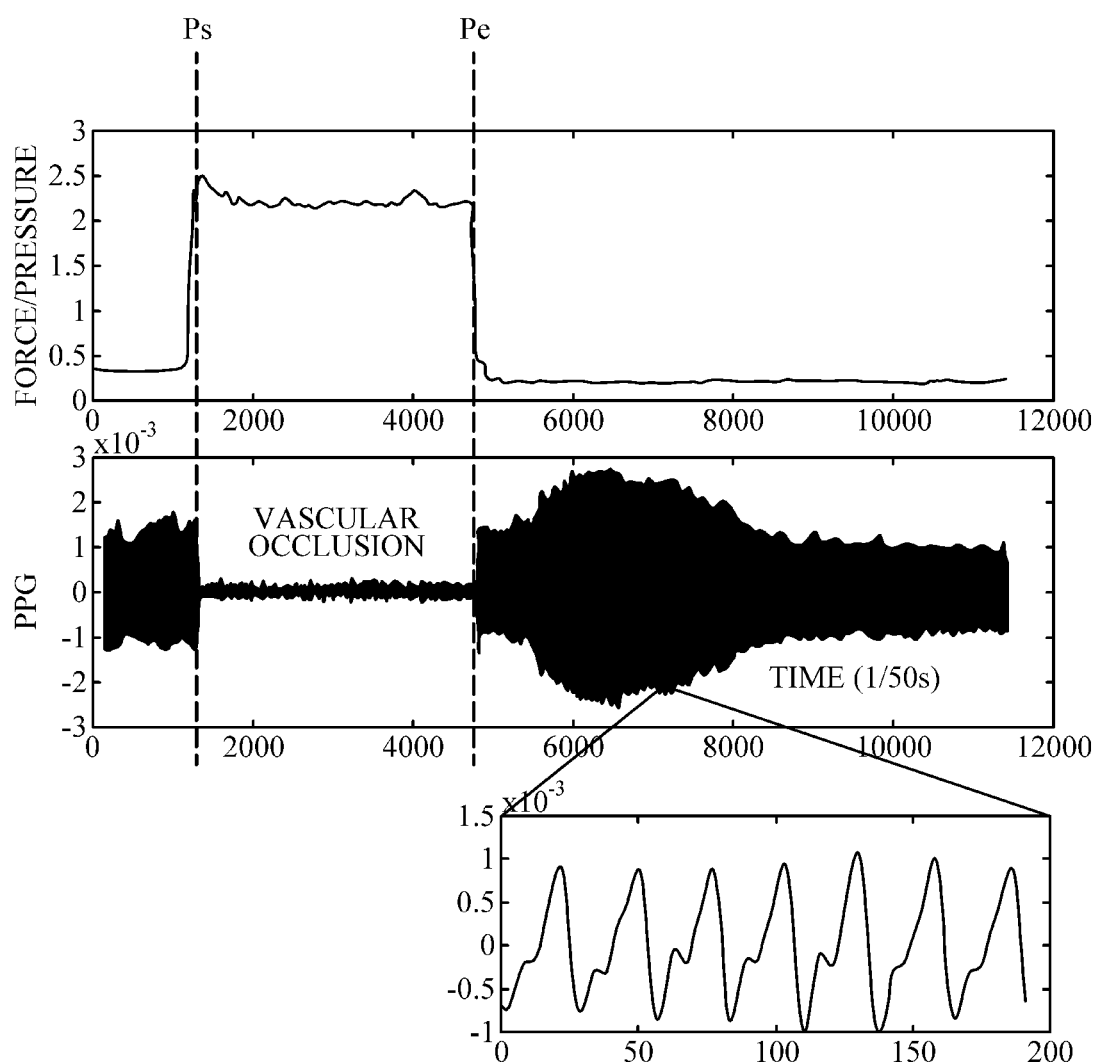
FIGS. 2A and 2B are diagrams illustrating photoplethysmography (PPG) signals before and after occlusion of blood vessels.
Figure 2B:
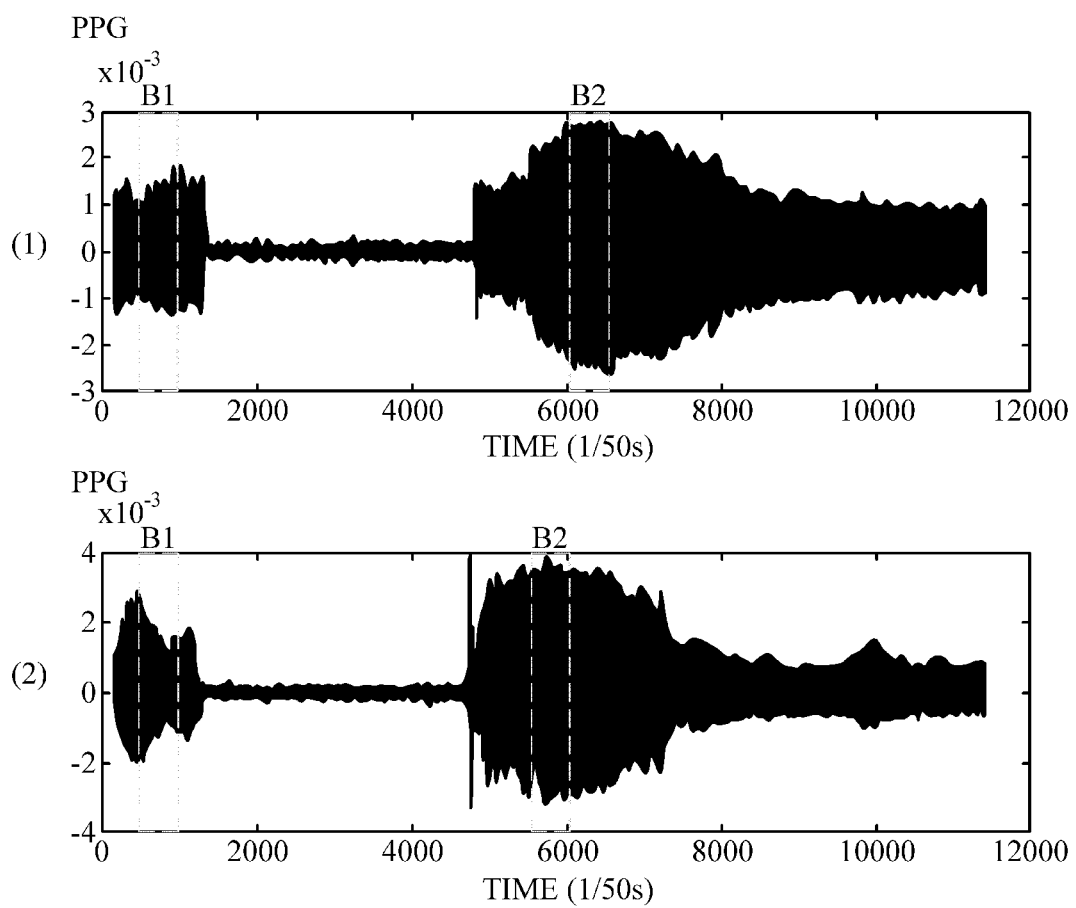

FIG. 1 is a block diagram illustrating an apparatus for monitoring health according to an example embodiment of the disclosure. FIGS. 2A and 2B are diagrams illustrating photoplethysmography (PPG) signals measured before and after occlusion of blood vessels.

An apparatus 100 for monitoring health according to an example embodiment is an apparatus for monitoring vascular health condition, and may be mounted in an electronic device, such as a smartphone, a tablet personal computer (PC), a desktop computer, a laptop computer, and the like, or in a medical device used in a medical institution. In addition, the apparatus 100 for monitoring health may be manufactured as an independent hardware device, such as a wearable device which is worn on an object and examples of which include a wristwatch-type wearable device, a bracelet-type wearable device, a wristband-type wearable device, a ring-type wearable device, a glasses-type wearable device, a headband-type wearable device, or the like, but the wearable device is not limited thereto.

Referring to FIG. 1, the apparatus 100 for monitoring health includes a pulse wave sensor 110 and a processor 120.

The pulse wave sensor 110 may measure a pulse wave signal, including a photoplethysmography (PPG) signal, from an object.

The object may be a part of a body which comes into contact with or is adjacent to the pulse wave sensor 110, and may be a part of a body from which pulse wave signals may be easily measured. For example, the object may be a skin area of a wrist which is adjacent to a radial artery, or a skin area of the body where veins or capillaries are located. However, the object is not limited thereto, and may be a distal portion of the body, such as a finger, a toe, and the like, where blood vessels are densely located.

The pulse wave sensor 110 may include a light source which emits light onto the object to detect an optical signal from the object based on the emitted light; and a detector which detects light emitted by the light source and is scattered or reflected from a body tissue such as a skin surface or blood vessels of the object. The light source may include a light emitting diode (LED), a laser diode (LD), a phosphor, and the like, but is not limited thereto. The detector may include a photo diode, a photo transistor (PTr), an image sensor (e.g., a complementary metal oxide semiconductor (CMOS) image sensor), and the like, but is not limited thereto. The pulse wave sensor 110 may have various structures, without a specific limitation, such as a structure including a plurality of light sources and one detector, or a structure including an array of pairs of light sources and detectors, and the like.

The pulse wave sensor 110 may measure a first pulse wave signal from an object in a first contact state under the control of the processor 120, and after a predetermined period of time elapses, the pulse wave sensor 110 may measure a second pulse wave signal from the object in a second contact state. The first contact state refers to a state before occlusion of blood vessels in an object, e.g., a finger, in which a user in a resting state touches the pulse wave sensor 110 with the finger and maintains a first pressure; and the second contact state refers to a state in which the user touches the pulse wave sensor 110 with the finger at the first pressure, gradually increases pressure to a second pressure or higher for occlusion of the blood vessels in the finger, and after a predetermined period of time elapses, the user gradually decreases pressure to maintain the first pressure again. The first contact state and/or the second contact state may further include information on a contact position, a contact time, and the like of the object.

For example, referring to FIG. 2A, an upper graph shows a force/pressure applied by the finger to the pulse wave sensor 110 over time, and a lower graph shows a pulse wave signal obtained by the pulse wave sensor 110 according to a change in the force/pressure applied by the finger to the pulse wave sensor 110 over time. When the finger is in contact with the pulse wave sensor 110 while maintaining the first pressure (e.g., an interval before Ps), the pulse wave sensor 110 may measure a first pulse wave signal; and when the finger applies the second pressure during a predetermined period of time (e.g., an interval from Ps to Pe) so that the blood vessels in the finger are occluded, and then decreases pressure so that the first pressure is maintained again (e.g., an interval after Pe), the pulse wave sensor 110 may measure a second pulse wave signal. The first pressure and/or the second pressure may be pre-defined values (e.g., default values) to be applied generally to a plurality of users, or may be values personalized (or determined) for each user by calibration.

In response to a request for monitoring health, the processor 120 may control the pulse wave sensor 110 to obtain the first pulse wave signal and the second pulse wave signal from the object. The request for monitoring health may be input by a user or may be generated at predetermined intervals. In response to the request for monitoring health, the processor 120 may perform a control operation to guide a user (e.g., output information to guide a user) to touch the pulse wave sensor 110 in the first contact state, and once the pulse wave sensor 110 obtains the first pulse wave signal based on the first contact state, the processor 120 may guide the user to touch the pulse wave sensor 110 in the second contact state.

In addition, when the processor 120 performs a control operation to guide the user on the first contact state, the processor 120 may monitor whether an alternating current (AC) component (e.g., corresponding to pulsatile) of the pulse wave signal is detected, and may guide the user on the first contact state again in a predetermined period of time. When the processor 120 performs the control operation to guide the user on the second contact state, and the object gradually increases pressure applied to the pulse wave sensor 110, the processor 120 may monitor whether an AC component of the pulse wave signal is detected. If the AC component is detected, the processor 120 may determine that the blood vessels are not yet occluded, and may increase the second pressure by a predetermined value and guide the user on the second contact state again based on the increased second pressure (e.g., output information to guide the user to gradually increase pressure to the increased second pressure or higher for occlusion of the blood vessels). Further, if the AC component of the pulse wave signal is not detected when the object increases pressure applied to the pulse wave sensor 110 to the increased second pressure or higher, the processor 120 may guide the user to decrease pressure and maintain the first pressure applied to the pulse wave sensor 110.

The PPG signal includes a pulsatile component (or an AC component) and a non-pulsatile or relatively slow varying component (or a direct current (DC) component). The AC component is related to the pulsating arteries and arterioles, and the DC component represents the constant absorption of non-pulsatile tissue (e.g., venous blood, venoules, non-pulsatile arterial blood, etc.).

Once the first pulse wave signal and the second pulse wave signal are obtained, the processor 120 may preprocess the first pulse wave signal and the second pulse wave signal. For example, the processor 120 may perform preprocessing, such as filtering for removing noise, amplifying the pulse wave signal, converting the signal into a digital signal, smoothing, and the like.

Based on the first pulse wave signal of the object, the processor 120 may estimate a first blood volume in a resting state before vascular occlusion, and based on the second pulse wave signal of the object, the processor 120 may estimate a second blood volume when blood is collected and then flows at once (e.g., after vascular occlusion).

FIG. 2B is a diagram illustrating an example of pulse wave signals obtained before and after vascular occlusion, in which a graph (1) shows an AC component of a pulse wave signal which is obtained from a finger before and after vascular occlusion while an upper arm is occluded and released by using a cuff; and a graph (2) shows an AC component of a pulse wave signal which is obtained from a finger by a pulse wave sensor mounted in a mobile device while the pulse wave sensor is pressed with the finger based on a guided pressure so that a blood flow in the finger is occluded and released. Referring to FIGS. 2A and 2B, it can be seen that a waveform of the pulse wave signal, which is obtained from the finger before and after vascular occlusion while an upper arm is occluded with a cuff, is similar to a waveform of the pulse wave signal which is obtained by the pulse wave sensor before and after vascular occlusion while the pulse wave sensor is pressed with the finger based on the guided pressure of the mobile device so that a blood flow of the finger is occluded. Based on the result, it can be estimated that when measured by using the cuff and the pulse wave sensor, a blood volume (B1) before vascular occlusion is changed in a similar manner to a blood volume (B2) when blood flows after vascular occlusion.

The processor 120 may extract a first AC component from the first pulse wave signal which is obtained from an object, e.g., finger, before vascular occlusion, and may estimate the first blood volume of blood flowing in the blood vessels before vascular occlusion based on the first AC component. For example, the processor 120 may extract a predetermined interval from the AC component of the first pulse wave signal before vascular occlusion. The predetermined interval may be an entire interval or a partial interval of the first pulse wave signal, and the partial interval may be a unit interval of a predetermined size. The processor 120 may extract the predetermined interval based on any point in a time interval of the first pulse wave signal, e.g., a middle point, a point where a pulse wave amplitude is maximum, and the like.

The processor 120 may obtain an area of the AC component in the extracted interval, and may estimate the first blood volume based on an area value of the AC component or a value obtained by properly adjusting the area of the AC component. For example, the processor 120 may calculate an average value of an AC component for the entire interval of the first pulse wave signal based on the calculated area of the AC component, and may estimate the calculated average value as the first blood volume. Likewise, the processor 120 may extract a second AC component from the second pulse wave signal obtained after occlusion of the blood vessels in the finger, and may estimate the second blood volume based on an area of the extracted second AC component in a predetermined interval. The predetermined interval may be an entire interval or a partial interval of the second pulse wave signal, as described above.

Upon obtaining the first blood volume and the second blood volume, the processor 120 may estimate a degree of vasodilation by using the first blood volume and the second blood volume. For example, the processor 120 may estimate the degree of vasodilation based on a difference between the first blood volume and the second blood volume, as represented by the following Equation 1, but is not limited thereto.

$$BD = \frac{AC_2 - AC_1}{AC_1} \times 100 \qquad \text{[Equation 1]}$$

Herein, BD denotes the estimated degree of vasodilation, and $AC_1$ and $AC_2$ denote the first blood volume and the second blood volume, respectively.

Upon estimating the degree of vasodilation, the processor 120 may monitor a vascular health condition based on the degree of vasodilation. For example, if the estimated degree of vasodilation is less than a predetermined threshold, the processor 120 may determine that there is an abnormality in the function of blood vessels. Upon determining that there is an abnormality in the function of blood vessels, the processor 120 may provide a user with information on predetermined actions to be taken in response to the determination, or may provide information on the determination result for related medical institutions, a related person in charge, and the like. However, the information is not limited thereto, and by using the estimated first blood volume and second blood volume, the degree of vasodilation, and the like, the processor 120 may estimate biometric information related to cardiovascular health, such as a blood pressure, a vascular age, an arterial stiffness, an aortic pressure waveform, a vascular compliance, a stress index, a fatigue level, and the like. In this case, the processor 120 may estimate bio-information by using a bio-information estimation model which defines a correlation between bio-information and the first blood volume, the second blood volume, the degree of vasodilation, and the like.

Figure 3:
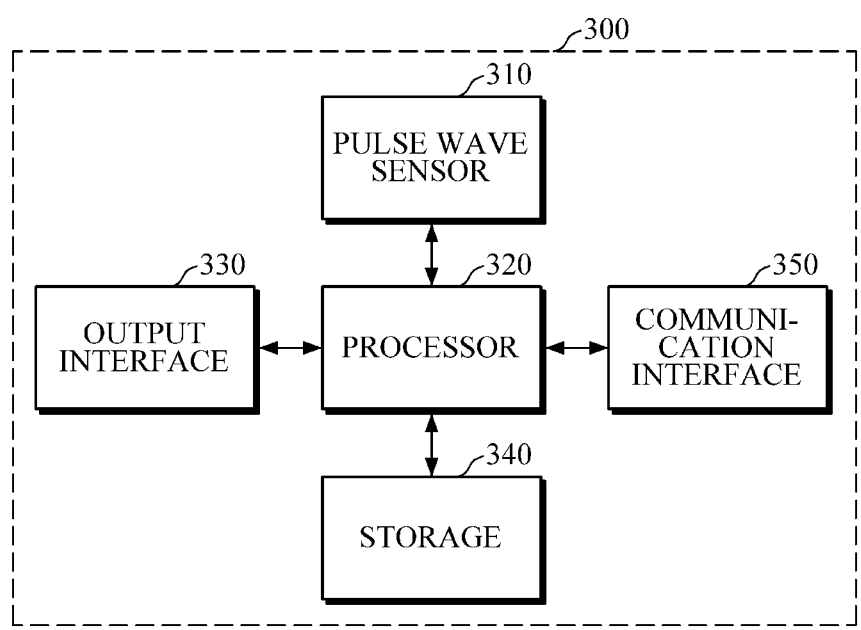
FIG. 3 is a block diagram illustrating an apparatus for monitoring health according to another example embodiment of the disclosure.

FIG. 3 is a block diagram illustrating an apparatus for monitoring health according to another example embodiment of the disclosure.

Referring to FIG. 3, an apparatus 300 for monitoring health according to an example embodiment includes a pulse wave sensor 310, a processor 320, an output interface 330, a storage 340, and a communication interface 350.

The pulse wave sensor 310 includes one or more light sources and one or more detectors, and may measure a pulse wave signal from an object.

The processor 320 may control the pulse wave sensor 310 to monitor a vascular health condition of a user, and may monitor a user's health condition by using the pulse wave signal obtained by the pulse wave sensor 310.

For example, in order to obtain a pulse wave signal before vascular occlusion of an object while a user is in a resting state, the processor 320 may perform an operation (e.g., output information) to guide the user on a first contact state, and when the pulse wave sensor 310 obtains the first pulse wave signal in the first contact state, the processor 320 may estimate a first blood volume based on an area of an AC component in a predetermined interval of the obtained first pulse wave signal. Further, in order to obtain a pulse wave signal after vascular occlusion, the processor 320 may perform an operation to guide the user on a second contact state, and when the pulse wave sensor 310 obtains the second pulse wave signal in the second contact state, the processor 320 may estimate a second blood volume based on an area of an AC component in a predetermined interval of the obtained second pulse wave signal.

Upon estimating the first blood volume before vascular occlusion and the second blood volume after vascular occlusion, the processor 320 may estimate a degree of vasodilation based on a difference between the estimated first blood volume and second blood volume, and may determine whether there is an abnormality in the function of blood vessels based on the estimated degree of vasodilation. For example, if the estimated degree of vasodilation is less than a predetermined threshold, the processor 320 may determine that there is an abnormality in the function of blood vessels, and may provide information related to the abnormality in the function of blood vessels based on the determination result.

The output interface 330 may provide processing results of the processor 320 by using a display, a speaker, and/or a haptic device, and the like.

For example, the output interface 330 may output a text and/or an image associated with the first contact state and the second contact state on a display under the control of the processor 320. Further, additionally or alternatively, along with or separately from the display, the output interface 330 may output a contact position or a contact pressure in the first contact state and the second contact state through a speaker using a voice signal. In addition, the output interface 330 may provide a user with information, including the determination result on an abnormality in the function of blood vessels, the predetermined actions to be taken in response to the determination result, and the like. In response to determination that there is an abnormality in the function of blood vessels, the output interface 330 may provide warning information on the abnormality to a user by properly using a visual method, such as color, font, thickness, and the like of a text, image, and the like, and a non-visual method such as tactile sensation, vibrations, voice, and the like.

The storage 340 may store processing results of the pulse wave sensor 310 and/or the processor 320. Further, the storage 340 may store a variety of reference information related to monitoring a health condition. For example, the reference information may include user characteristic information such as a user's age, sex, presence or absence of a disease, types of diseases, and the like. In addition, the reference information may include one or more estimation models, thresholds, and the like. However, the information is not limited thereto.

The storage 340 may include at least one storage medium of a flash memory type memory, a hard disk type memory, a multimedia card micro type memory, a card type memory (e.g., a secure digital (SD) memory, an extreme digital (XD) memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like, but is not limited thereto.

The communication interface 350 may communicate with an external device by using wired or wireless communication techniques, and may transmit and receive various data to and from the external device. For example, the communication interface 350 may transmit information, such as the determination result and/or the predetermined actions in response to the determination result, and the like to the external device. For example, the communication interface 350 may transmit the determination result and/or the predetermined actions to a user's smartphone, tablet PC, desktop computer, and laptop computer, a server of a medical institution, and the like. In addition, the communication interface 350 may transmit a text message, including the determination result and/or the predetermined actions, to a mobile terminal of a person in charge of a medical institution or a user's protector.

Examples of the communication techniques may include Bluetooth communication, Bluetooth low energy (BLE) communication, near field communication (NFC), wireless local access network (WLAN) communication, Zigbee communication, infrared data association (IrDA) communication, wireless fidelity (Wi-Fi) direct (WFD) communication, ultra-wideband (UWB) communication, Ant+ communication, Wi-Fi communication, radio frequency identification (RFID) communication, third generation (3G), fourth generation (4G), and fifth generation (5G) telecommunications, and the like. However, these are merely examples and are not intended to be limiting, FIG. 4 is a block diagram illustrating an apparatus for monitoring health according to yet another example embodiment of the disclosure.

Figure 4:
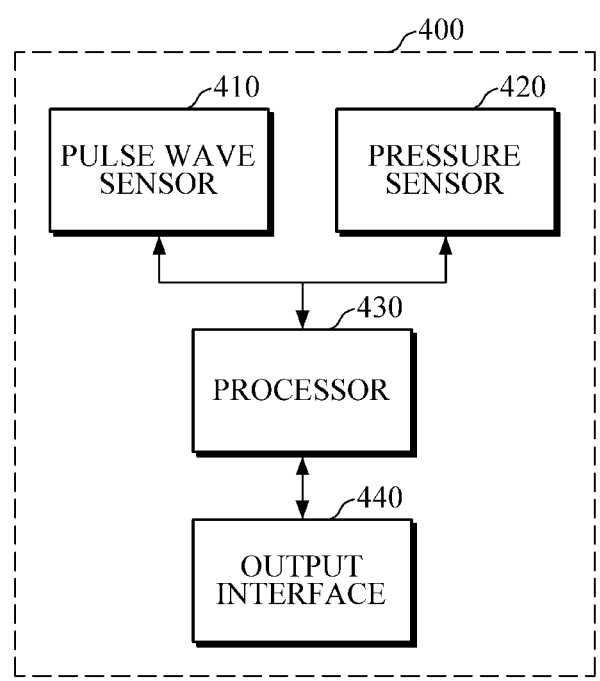
FIG. 4 is a block diagram illustrating an apparatus for monitoring health according to yet another example embodiment of the disclosure.

Referring to FIG. 4, an apparatus 400 for monitoring health according to an example embodiment includes a pulse wave sensor 410, a pressure sensor 420, a processor 430, and an output interface 440.

The pulse wave sensor 410 includes one or more light sources and one or more detectors, and may measure a pulse wave signal from an object of a user.

The pressure sensor 420 may measure a contact pressure between the object and the pulse wave sensor 410 when the object is in contact with the pulse wave sensor 410.

The processor 430 may control the puke wave sensor 410 to monitor a user's vascular health condition, and may monitor a user's health condition by using the pulse wave signal obtained by the pulse wave sensor 410.

For example, in order to obtain a pulse wave signal before vascular occlusion of the object while the user is in a resting state, the processor 430 may perform an operation (e.g., provide information) to guide the user on a first contact state. The processor 430 may receive a contact pressure of the object from the pressure sensor 420 when the object is in contact with the pulse wave sensor 410, and may perform an operation to guide the first contact state based on the received contact pressure. For example, by comparing the first pressure in the first contact state, provided for the user, with an actual contact pressure received from the pressure sensor 420, the processor 430 may perform an operation to guide the user in real time to increase or decrease a contact pressure of the object. In other words, the processor 430 may perform an operation to guide the user to increase a contact pressure based on a determination that the contact pressure received from the pressure sensor 420 is less than the first pressure, and to decrease the contact pressure based on a determination that the contact pressure received from the pressure sensor 420 is greater than the first pressure.

The processor 430 may perform an operation to guide the user on a second contact state. Likewise, by comparing the second pressure, provided for occlusion of the blood vessels, with the actual contact pressure measured by the pressure sensor 420, the processor 430 may perform an operation to guide the user in real time to increase or decrease contact pressure of the object. Upon determining that the blood vessels are occluded based on the actual contact pressure received from the pressure sensor 420, the processor 430 may perform an operation to guide the user to decrease the contact pressure to the first pressure, and to maintain the first pressure based on the actual contact pressure received from the pressure sensor 420.

As described above, by guiding the first contact state or the second contact state, and by considering whether to detect an AC component of the pulse wave signal in the first contact state and/or the second contact state along with the actual contact pressure detected by the pressure sensor 420, the processor 430 may guide the user to maintain an optimal contact state before and after vascular occlusion.

A reference pressure may be a value of the first pressure corresponding to the first contact state or the second pressure corresponding to the second contact state. The reference pressure may have a value that is generally applied to a plurality of users, or may have a personalized value obtained for each user at a calibration time.

For example, in response to a request for calibration, the processor 430 may update information on the first contact state and/or the second contact state by performing calibration for a specific user. The reference pressure may be preset as a value which may be generally applied at a time of manufacturing the apparatus 400 for monitoring health. Thereafter, the processor 430 may determine a reference pressure, personalized for a user, by performing calibration at a time when the user registers user information to use the apparatus 400 for monitoring health, at a time when the user requests calibration for changing an object or based on a change in health condition, and the like, or by performing calibration at predetermined intervals.

For example, in order to determine a first pressure corresponding to a first contact state at a calibration time, the processor 430 may perform an operation to guide a user not to apply a force while the object is in contact with the pulse wave sensor 410. If an AC component is not detected from the pulse wave signal after the contact of the object, the processor 430 may perform an operation to guide the user to gradually increase a pressing force, and if the AC component of the pulse wave signal is detected as the user gradually increases force, the processor 430 may determine a contact pressure, measured by the pressure sensor 420 at the time of detecting the AC component, as the first pressure personalized for the user.

Further, in order to determine a second pressure corresponding to a second contact state, the processor 430 may perform an operation to guide the user to increase a contact pressure to a predetermined pressure. The predetermined pressure may be a preset pressure value (e.g., a default second pressure value corresponding to the second contact state) which may be generally used or a systolic blood pressure value of the user, but is not limited thereto. When the user gradually increases a pressing force to the predetermined pressure while pressing the pulse wave sensor 410 with the object, if the AC component of the pulse wave signal is detected, the processor 430 may perform an operation to guide the user to again increase the contact pressure to be greater than the predetermined pressure. The above process is repeated until when the AC component of the pulse wave signal stops to be detected, upon which the processor 430 may determine that the blood vessels in the object are occluded, and may determine the contact pressure, measured by the pressure sensor 420 at that time, as a second pressure personalized for the user.

Once the pulse wave sensor 410 obtains the first pulse wave signal in the first contact state, the processor 430 may estimate a first blood volume based on an area of a first AC component in a predetermined interval of the obtained first pulse wave signal. Further, the processor 430 may perform an operation to guide a user on a second contact state to obtain a pulse wave signal after vascular occlusion. Once the pulse wave sensor 410 obtains the second pulse wave signal in the second contact state, the processor 430 may estimate a second blood volume based on an area of a second AC component in a predetermined interval of the second pulse wave signal.

In addition, based on a difference between the reference pressure and the actual contact pressure measured by the pressure sensor 420, the processor 430 may correct an area of the AC component of the pulse wave signal measured by the pulse wave sensor 410. For example, based on a difference between the first pressure corresponding to the first contact state and an actual contact pressure at a measurement time of the first pulse wave signal, the processor 430 may correct the area of the first AC component by applying a predefined first correction value calculation equation. Likewise, based on a difference between the first pressure and an actual contact pressure at a measurement time of the second pulse wave signal, the processor 430 may correct the area of the second AC component by applying a pre-defined second correction value calculation equation.

Upon estimating the first blood volume before vascular occlusion and the second blood volume after vascular occlusion, the processor 430 may estimate a degree of vasodilation based on a variation between the estimated first blood volume and second blood volume, and may determine whether there is an abnormality in the function of blood vessels based on the estimated degree of vasodilation. For example, if the estimated degree of vasodilation is less than a predetermined threshold, the processor 430 may determine that there is an abnormality in the function of blood vessels, and may provide guide information based on the determination result.

The output interface 440 may provide processing results of the processor 430 by using a display, a speaker, and/or a haptic device, and the like. The output interface 440 may output guide information on the first contact state and/or the second contact state according to a guiding operation by the processor 430. The output interface 440 may output the actual contact pressure value, measured by the pressure sensor 420, and the reference pressure (e.g., the first pressure or the second pressure) at the same time so that the pressure values may be visually compared, or may output information indicating whether the contact pressure measured by the pressure sensor 420 needs to increase or decrease based on a difference between the reference pressure and the measured contact pressure. Further, as described above, the output interface 440 may output health monitoring information related to the function of blood vessels.

Figure 5:
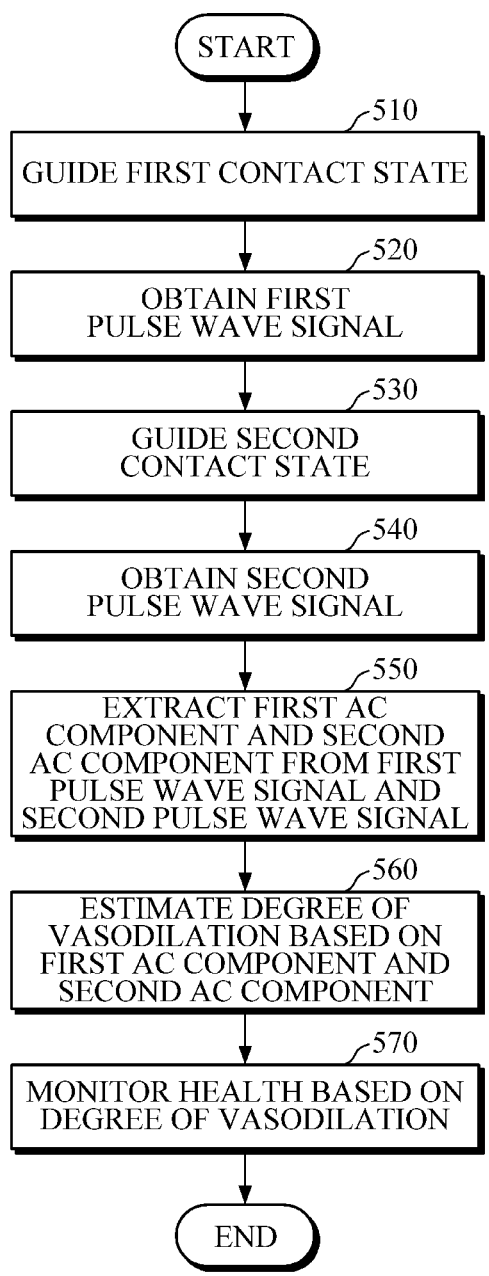
FIG. 5 is a flowchart illustrating a method of monitoring health according to an example embodiment of the disclosure.

FIG. 5 is a flowchart illustrating a method of monitoring health according to an example embodiment of the disclosure. FIG. 5 is an example of a method of monitoring health which may be performed by any one of the apparatuses 100 and 300 for monitoring health according to the example embodiments of FIGS. 1 and 3. Detailed description of the apparatuses 100 and 300 is given above, and thus repetitive description will be avoided.

Referring to FIG. 5, the apparatus for monitoring health may guide a user on a first contact state in 510 The first contact state refers to a state for measuring a pulse wave signal before occlusion of blood vessels in an object when a user in a resting state, and may include information on a contact position and/or a first pressure, and the like. The first pressure refers to a minimum contact pressure, at which an AC component of the pulse wave signal is detected when the object is in contact with the pulse wave sensor while applying little force.

Then, the apparatus for monitoring health may obtain a first pulse wave signal in the first contact state of the object by using the pulse wave sensor in 520. The apparatus for monitoring health may monitor whether an AC component of the first pulse wave signal is detected before vascular occlusion, and if the AC component of the first pulse wave signal is not detected or verified, the apparatus for monitoring health may perform operation 510 again.

Subsequently, once the first pulse wave signal is obtained, the apparatus for monitoring health may guide a second contact state in 530. The second contact state refers to a state in which the contact pressure by an object is increased to a second pressure or higher so that the blood vessels in the object may be occluded, and when a predetermined period of time elapses after the blood vessels are occluded, the contact pressure is decreased to the first pressure and maintained at the first pressure.

Next, the apparatus for monitoring health may obtain a second pulse wave signal in the second contact state of the object by using the pulse wave sensor in 540. In this case, after guiding the second pressure, the apparatus for monitoring health may verify if the AC component of the pulse wave signal is not detected so as to identify the occlusion of the blood vessels, and if the pulse wave signal is continuously detected, the apparatus for monitoring health may guide a user to increase the contact pressure to be greater than the second pressure.

Then, the apparatus for monitoring health may extract a first AC component and a second AC component from the first pulse wave signal and the second pulse wave signal, respectively, in 550, and may estimate a degree of vasodilation based on the extracted first AC component and second AC component in 560. The apparatus for monitoring health may obtain an area of the first AC component in a predetermined interval and may estimate a first blood volume based on the obtained area. Further, the apparatus for monitoring health may obtain an area of the second AC component in a predetermined interval and may estimate a second blood volume based on the obtained area. In addition, the apparatus for monitoring health may estimate the degree of vasodilation based on a difference between the first blood volume and the second blood volume.

Subsequently, the apparatus for monitoring health may monitor a vascular health condition based on the degree of vasodilation in 570. For example, if the estimated degree of vasodilation is less than a predetermined threshold, the apparatus for monitoring health may determine that there is an abnormality in the function of blood vessels, and may perform one or more predetermined operations. For example, the apparatus for monitoring health may provide a user with guide information, such as a determination result, health condition, and/or predetermined actions to be taken in response to the determination result, and the like, or may transmit a text message including the information to related medical institutions, a related person in charge, and the like, to provide information on a user's health condition.

Figure 6:
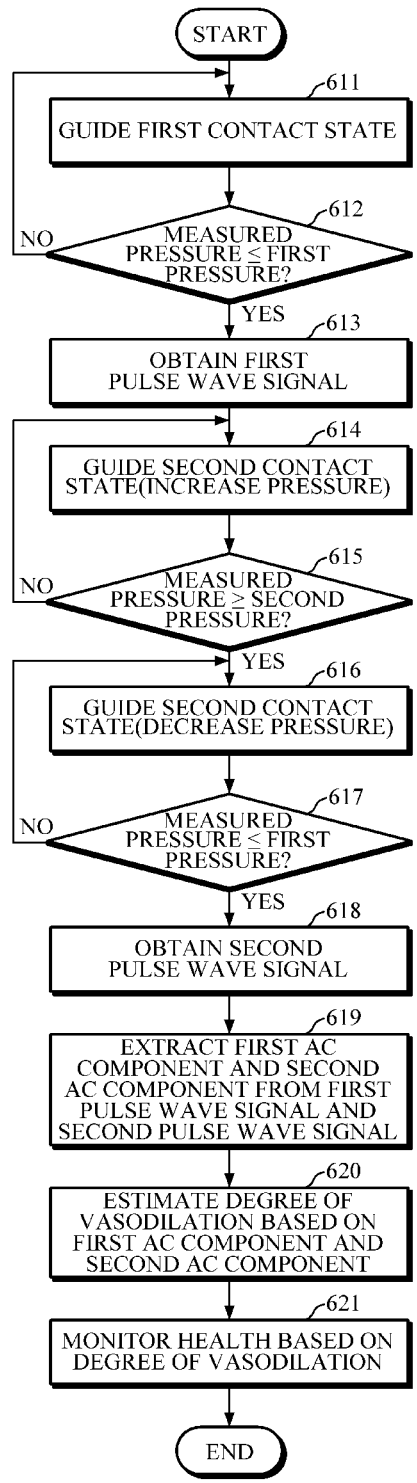
FIG. 6 is a flowchart illustrating a method of monitoring health according to another example embodiment of the disclosure.

FIG. 6 is a flowchart illustrating a method of monitoring health according to another example embodiment of the disclosure.

FIG. 6 is an example of a method of monitoring health which may be performed by the apparatus 400 for monitoring health according to the example embodiment of FIG. 4.

Referring to FIG. 6, the apparatus 400 for monitoring health may guide a user on a first contact state based on a first pressure in 611. When an object comes into contact with a pulse wave sensor in the first contact state according to guiding of the apparatus 400, the apparatus 400 for monitoring health may compare an actual pressure, measured by a pressure sensor when the object is in contact with the pulse wave sensor in the first contact state, with the first pressure corresponding to the first contact state in 612. Upon comparison, if the measured actual pressure exceeds the first pressure, the apparatus 400 for monitoring health may return to 611 and again guide the user to apply the first pressure to be in the first contact state.

If the measured actual pressure is determined to be less than or equal to the first pressure in 612, the apparatus 400 for monitoring health may obtain a first pulse wave signal by using the pulse wave sensor in 613.

Next, once the first pulse wave signal is obtained in the first contact state in 613, the apparatus 400 for monitoring health may guide a second pressure in a second contact state in 614, so that the blood vessels in the object may be occluded, and may monitor whether the blood vessels in the object are occluded by comparing the actual pressure, measured by the pressure sensor, with the second pressure in 615. Upon comparison, if the measured actual pressure is not greater than or equal to the second pressure, the apparatus 400 for monitoring health may determine that the blood vessels are not occluded, and may perform operation 614 again to guide the second pressure in the second contact state.

If the measured actual pressure is determined to be greater than or equal to the second pressure in 615, the apparatus 400 for monitoring health may determine that the blood vessels are occluded, and may guide the user to decrease the contact pressure and to maintain the first pressure in 616.

Then, the apparatus 400 for monitoring health may compare the actual pressure, measured by the pressure sensor, with the first pressure in 617. Upon comparison, if the measured actual pressure exceeds the first pressure, the apparatus 400 for monitoring health may guide the user again to maintain the first pressure according to the second contact state in 616.

Subsequently, upon comparison in 617, if the actual contact pressure of the object is maintained to be less than or equal to the first pressure, the apparatus 400 for monitoring health may obtain a second pulse wave signal by using the pulse wave sensor in 618.

Next, the apparatus 400 for monitoring health may extract a first AC component and a second AC component from the first pulse wave signal and the second pulse wave signal, respectively, in 619, and may estimate a degree of vasodilation based on the extracted first AC component and second AC component in 620. The apparatus 400 for monitoring health may estimate a first blood volume and a second blood volume based on an area of the first AC component and an area of the second AC component in a predetermined interval, and may estimate a degree of vasodilation based on a difference between the first blood volume and the second blood volume. In this case, based on a difference between the actual contact pressure, measured by the pressure sensor at a time when the first pulse wave signal and the second pulse wave signal are obtained, and the first pressure, the apparatus 400 for monitoring health may correct the area of the first AC component and the area of the second AC component.

Then, the apparatus 400 for monitoring health may monitor a vascular health condition based on the degree of vasodilation in 621. For example, if the degree of vasodilation is less than a predetermined threshold, the apparatus 400 for monitoring health may determine that there is an abnormality in the function of blood vessels, and may perform predetermined actions based on the determination result.

Figure 7:
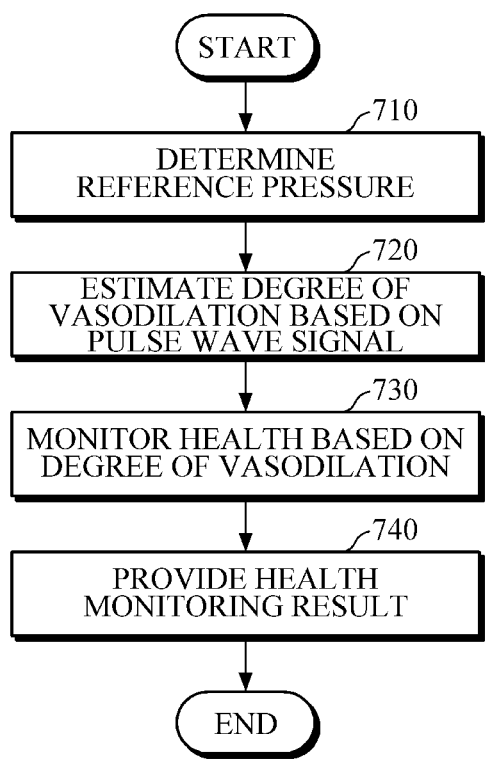
FIG. 7 is a flowchart illustrating a method of monitoring health according to yet another example embodiment of the disclosure.
Figure 8:
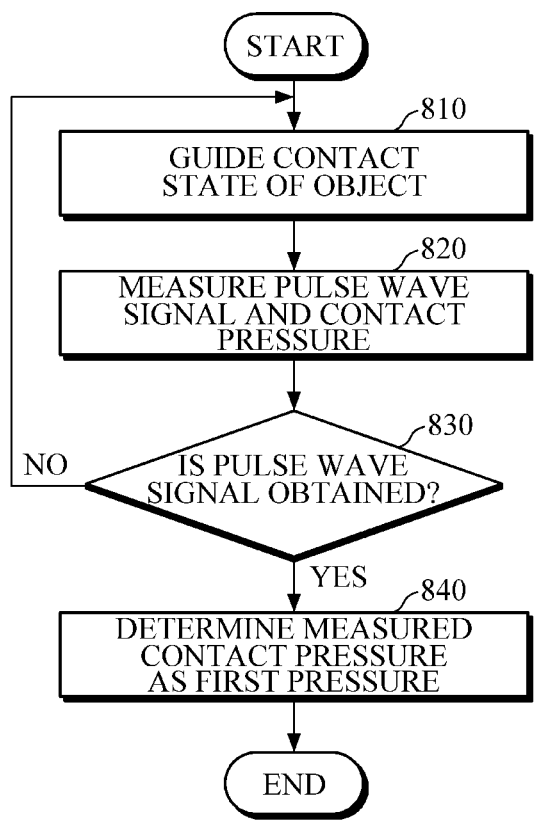
FIG. 8 is a flowchart illustrating an example of determining reference pressure of FIG. 7.
Figure 9:
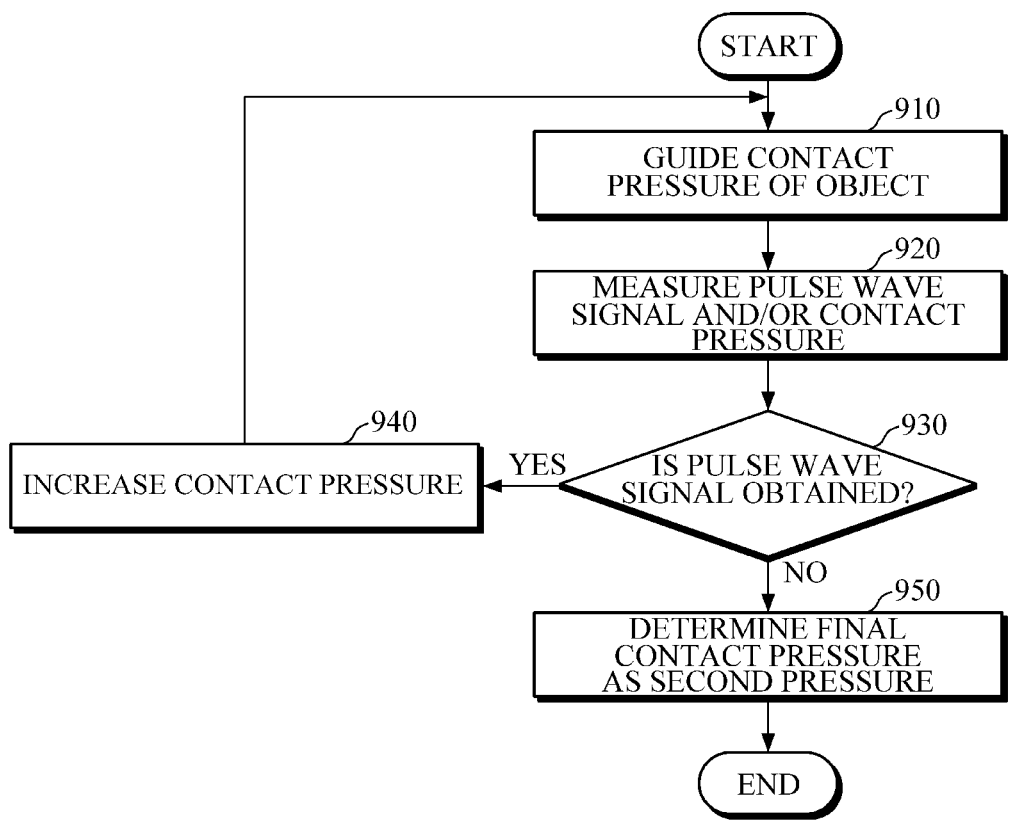
FIG. 9 is a flowchart illustrating another example of determining reference pressure of FIG. 7.

FIG. 7 is a flowchart illustrating a method of monitoring health according to yet another example embodiment of the disclosure. FIG. 8 is a flowchart illustrating an example of determining reference pressure of FIG. 7. FIG. 9 is a flowchart illustrating another example of determining reference pressure of FIG. 7. The methods of FIGS. 7 to 9 may be examples performed by the apparatus 400 for monitoring health of FIG. 4, which will be briefly described below.

The apparatus 400 for monitoring health may determine a reference pressure (e.g., a first pressure and a second pressure) in 710.

For example, referring to FIG. 8, the apparatus 400 for monitoring health may determine a first pressure for obtaining a pulse wave signal before vascular occlusion while an object is in a resting state.

The apparatus 400 for monitoring health may guide a contact state of the object in 810. For example, while the object is in contact with the pulse wave sensor, the apparatus 400 for monitoring health may guide the object not to apply force.

Then, the apparatus 400 for monitoring health may measure a pulse wave signal and a contact pressure by using a pulse wave sensor and a pressure sensor in 820.

Subsequently, if a pulse wave signal is not obtained from the object in a current contact state in 830, the apparatus 400 for monitoring health may repeat operation 810 to guide the user to slightly increase or decrease a pressing force applied by the object to the pulse wave sensor, and repeat operation 820 to measure the pulse wave signal and the contact pressure.

Next, once the pulse wave signal is obtained in operations 810 to 830, the apparatus 400 for monitoring health may determine the contact pressure at the time of obtaining the pulse wave signal as the first pressure in the first contact state in 840. In this manner, the apparatus 400 for monitoring health may determine a first pressure in the first contact state which is personalized for each user or for each object of the user by reflecting a user characteristic.

In another example, referring to FIG. 9, the apparatus 400 for monitoring health may determine a second pressure for obtaining a pulse wave signal after occlusion of the blood vessels in the object.

The apparatus 400 for monitoring health may guide a user on a predetermined contact pressure of an object in 910. The predetermined contact pressure may have a pre-defined pressure value which may be generally used or a systolic blood pressure value of the user, but is not limited thereto.

Then, the apparatus 400 for monitoring health may measure a pulse wave signal and a contact pressure by using a pulse wave sensor and a pressure sensor in 920.

Subsequently, if the pulse wave signal is obtained while the predetermined contact pressure is applied in 930, the apparatus 400 for monitoring health may determine that the blood vessels are not yet occluded, and may increase the predetermined contact pressure by a predetermined value (e.g., 0.5) in 940, and may return to operation 910 to guide the user to apply the increased predetermined contact pressure.

Next, if the pulse wave signal is not obtained in 930, the apparatus 400 for monitoring health may determine the contact pressure, measured in 920, as a second pressure in 950. Pressure required for occlusion of the blood vessels may be different for each user or for each object of the user, such that by repeating operations 910 to 930, the apparatus 400 for monitoring health may determine the second pressure which is personalized for each user or for each object of the user.

Referring back to FIG. 7, in response to a request for monitoring a vascular health condition, the apparatus 400 for monitoring health may obtain the first pulse wave signal and the second pulse wave signal based on the reference pressure determined in 710, and may estimate a degree of vasodilation based on the obtained first pulse wave signal and second pulse wave signal in 720. Then, the apparatus 400 for monitoring health may monitor a health condition based on the degree of vasodilation in 730. Subsequently, the apparatus 400 for monitoring health may provide a health monitoring result for the user in 740.

Figure 10:
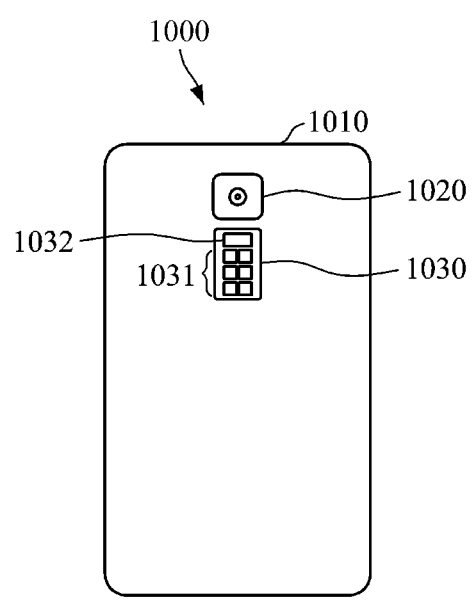
FIGS. 10 and 11 are diagrams illustrating a mobile device according to an example embodiment of the disclosure.
Figure 11:
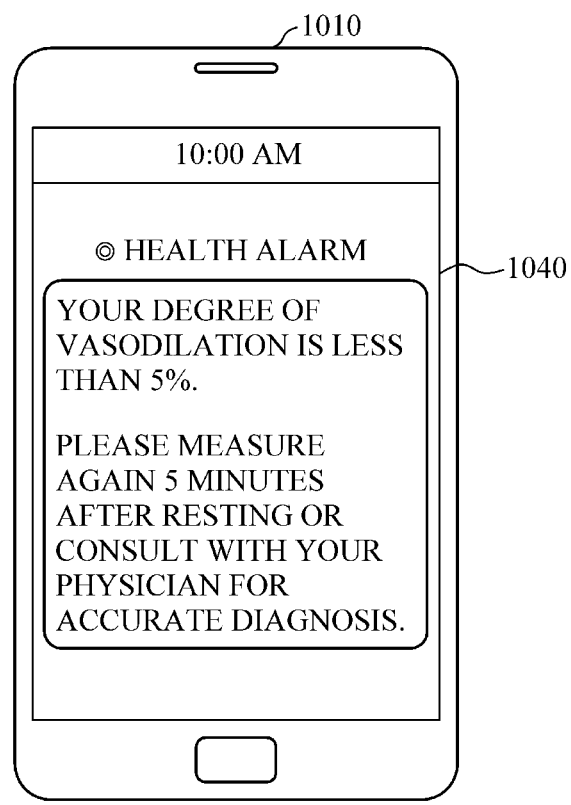

FIGS. 10 and 11 are diagrams illustrating a mobile device according to an example embodiment of the disclosure.

As illustrated in FIGS. 10 and 11, the mobile device 1000 may be a smartphone and a tablet PC which may be carried by a user, but is not limited thereto, and may be a wearable device which may be worn on a user's body part.

Referring to FIG. 10, the mobile device 1000 includes a main body 1010 and a sensor part (or a sensor) 1030 which is disposed on one surface of the main body 1010. The sensor part 1030 includes a pulse wave sensor including one or more light sources 1031 and a detector 1032. As illustrated in FIG. 10, the sensor part 1030 may be mounted on a rear surface of the main body 1010, but is not limited thereto, and may be configured in combination with a fingerprint sensor or a touch panel mounted on a front surface of the main body 1010.

In addition, a display 1040 may be mounted on a front surface of the main body 1010. The display 1040 may visually display a health monitoring result and the like. The display 1040 may include a touch panel, and may receive a variety of information input through the touch panel and transmit the received information to the processor.

Moreover, an image sensor 1020 may be mounted in the main body 1010. When a user's finger approaches the sensor part 1030 to measure a pulse wave signal, the image sensor 1020 may capture an image of the finger and may transmit the captured image to the processor. In this case, based on the image of the finger, the processor may identify a relative position of the finger with respect to an actual position of the sensor part 1030, and may provide the relative position of the finger for the user through the display, so as to guide measurement of pulse wave signals with improved accuracy.

The processor may be electrically connected to the sensor part 1030, and may control the sensor part 1030 in response to a request for monitoring vascular health. In order to obtain a pulse wave signal from an object before occlusion of the blood vessels in the object, the processor may perform an operation to guide a user to touch the sensor part 1030 with the object with a first pressure. Further, in order to obtain a pulse wave signal when the blood vessels are opened again after occlusion of the blood vessels in the object, the processor may perform an operation to guide the user to touch the sensor part 1030 with the object with a second pressure, and when a predetermined period of time elapses and/or when a predetermined condition is met (e.g., occlusion of the blood vessels is identified), the processor may perform an operation to guide the user to touch the sensor part 1030 with the first pressure again.

Based on an area of an AC component of each pulse wave signal obtained before and after occlusion of the blood vessels, the processor may estimate a degree of vasodilation, and may monitor a vascular health condition based on the estimated degree of vasodilation. For example, if the estimated degree of vasodilation is less than a predetermined threshold, the processor may determine that there is an abnormality in the function of blood vessels, and may display health monitoring information, including actions in response to the determination result, through the display 1040 as illustrated in FIG. 11.

Further, a communication interface for communication with a mobile terminal of a user or a protector of the user and an external device such as a server of a medical institution. The communication interface may transmit a health monitoring result to an external device, so that prompt actions may be taken for the user.

In addition, a storage may be mounted in the main body 1010, and the processor may store processing results in the storage. Furthermore, a variety of information related to various functions of a smart device may be stored in the storage.

The disclosure can be realized as a computer-readable code written on a computer-readable recording medium. The computer-readable recording medium may be any type of recording device in which data is stored in a computer-readable manner.

Examples of the computer-readable recording medium include a ROM, a RAM, a compact disc (CD)-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Also, functional programs, codes, and code segments for implementing the disclosure can be readily construed by programmers of ordinary skill in the art, to which the disclosure pertains.

The foregoing embodiments are merely intended for describing the technical solutions, but not for limiting the disclosure. Although the disclosure is described in detail with reference to the foregoing embodiments, persons of ordinary skill in the art should understand that they may still make modifications to the technical solutions described in the foregoing embodiments or make equivalent replacements to some technical features thereof, without departing from the spirit and scope of the technical solutions of the embodiments.

What is claimed is:

1. An apparatus for non-invasively monitoring a vascular health condition, the apparatus comprising:
   a pulse wave sensor configured to:
      obtain a first pulse wave signal at a first time in a first contact state of an object, wherein the first contact state is a state in which the object touches the pulse wave sensor at a contact pressure of a first pressure and maintains the contact pressure of the first pressure; and
      obtain a second pulse wave signal at a second time in a second contact state of the object, wherein the second contact state is a state in which, after the object touches the pulse wave sensor at the contact pressure of the first pressure, gradually increases the contact pressure to a second pressure or higher, and upon satisfaction of a condition, gradually decreases the contact pressure to the first pressure, the object maintains the contact pressure of the first pressure;
   a pressure sensor configured to obtain the contact pressure of the object that comes into contact with the pulse wave sensor;
   an image sensor configured to capture an image of the object that approaches the pulse wave sensor to obtain the first pulse wave signal and/or the second pulse wave signal;
   a display configured to, based on the captured image of the object, display a relative position of the object with respect to a position of the pulse wave sensor; and
   a processor configured to:
      correct an area of a first alternating current (AC) component of the first pulse wave signal based on a difference, obtained by using the pressure sensor, between a contact pressure of the object at the first time of obtaining the first pulse wave signal and the first pressure corresponding to the first contact state;
      correct an area of a second AC component of the second pulse wave signal based on a difference, obtained by using the pressure sensor, between a contact pressure of the object at the second time of obtaining the second pulse wave signal and the second pressure corresponding to the second contact state; and
      estimate a first blood volume based on the corrected area of the first AC component, estimate a second blood volume based on the corrected area of the second AC component, estimate a degree of vasodilation based on a difference between the first blood volume and the second blood volume, and output a result of a vascular health condition based on the estimated degree of vasodilation, wherein, based on a request, the processor is further configured to:
provide information on the first contact state to a user to guide the user to touch the pulse wave sensor with the object at the contact pressure of the first pressure; and
provide information on the second contact state to the user to guide the user to increase the contact pressure to the second pressure or higher, and upon the satisfaction of the condition, to decrease the contact pressure to the first pressure.

2. The apparatus of claim 1, wherein the pulse wave sensor comprises:
a light source configured to emit light onto the object; and
a detector configured to detect light reflected or scattered from the object.

3. The apparatus of claim 1, wherein upon providing the information on the first contact state, in response to the AC component of the first pulse wave signal not being detected, the processor is further configured to again provide the information on the first contact state to the user.

4. The apparatus of claim 1, wherein upon providing the information on the second contact state, in response to the AC component of the second pulse wave signal being detected, the processor is further configured to increase a value of the second pressure and provide the information on the second contact state with the second pressure having the increased value.

5. The apparatus of claim 1, wherein the processor is further configured to provide the information on the first contact state and the second contact state based on the contact pressure of the object which is obtained by the pressure sensor.

6. The apparatus of claim 1, wherein each of the first pressure and the second pressure has at least one of a preset value, or a value determined for the user.

7. The apparatus of claim 6, wherein the processor is further configured to determine the value of the first pressure by providing information to guide the user to touch the pulse wave sensor with the object in a resting state, and determining the value of the first pressure based on whether the AC component of the first pulse wave signal is detected while the object is in contact with the pulse wave sensor in the resting state.

8. The apparatus of claim 6, wherein the processor is further configured to determine the value of the second pressure by providing information to guide the user to increase the contact pressure to a predetermined pressure or greater, and determining the value of the second pressure based on whether the AC component of the second pulse wave signal is detected at the contact pressure increased to the predetermined pressure or greater.

9. The apparatus of claim 1, wherein in response to the estimated degree of vasodilation being less than a predetermined threshold, the processor is further configured to determine an abnormality in a function of a blood vessel.

10. The apparatus of claim 1, further comprising an output interface configured to output the result of monitoring the vascular health condition.

11. A method of non-invasively monitoring a vascular health condition, performed by an apparatus including a pulse wave sensor, a pressure sensor, an image sensor, a display, and a processor, the method comprising:
obtaining, by the pulse wave sensor, a first pulse wave signal at a first time in a first contact state of an object, wherein the first contact state is a state in which the object touches the pulse wave sensor at a contact pressure of a first pressure and maintains the contact pressure of the first pressure;
obtaining, by the pulse wave sensor, a second pulse wave signal at a second time in a second contact state of the object, wherein the second contact state is a state in which, after the object touches the pulse wave sensor at the contact pressure of the first pressure, gradually increases the contact pressure to a second pressure or higher, and upon satisfaction of a condition, gradually decreases the contact pressure to the first pressure, the object maintains the contact pressure of the first pressure;
correcting an area of a first alternating current (AC) component of the first pulse wave signal based on a difference, obtained by using the pressure sensor, between a contact pressure of the object at the first time of obtaining the first pulse wave signal and the first pressure corresponding to the first contact state;
correcting an area of a second AC component of the second pulse wave signal based on a difference, obtained by using the pressure sensor, between a contact pressure of the object at the second time of obtaining the second pulse wave signal and the second pressure corresponding to the second contact state; and
estimating a first blood volume based on the corrected area of the first AC component, estimating a second blood volume based on the corrected area of the second AC component, estimating a degree of vasodilation based on a difference between the first blood volume and the second blood volume, and outputting a result of a vascular health condition based on the estimated degree of vasodilation,
wherein in the obtaining the first pulse wave signal and/or the second pulse wave signal, the method further comprises:
capturing, by using the image sensor, an image of the object that approaches the pulse wave sensor to obtain the first pulse wave signal and/or the second pulse wave signal;
controlling the display to display, based on the captured image of the object, a relative position of the object with respect to a position of the pulse wave sensor; and
based on a request providing information on the first contact state to a user to guide the user to touch the pulse wave sensor with the object with the contact pressure of the first pressure, and providing information on the second contact state to the user to guide the user to increase the contact pressure to the second pressure or higher, and upon the satisfaction of the condition, to decrease the contact pressure to the first pressure.

12. The method of claim 11, further comprising:
upon providing the information on the first contact state, in response to the AC component of the first pulse wave signal not being detected, again providing the information on the first contact state to the user.

13. The method of claim 11, further comprising:
upon providing the information on the second contact state, in response to the AC component of the second pulse wave signal being continuously detected, increasing a value of the second pressure and providing the information on the second contact state with the second pressure having the increased value.

14. The method of claim 11, wherein the providing the information on the first contact state and the second contact state comprises providing the information on the first contact state and the second contact state based on the contact pressure of the object obtained by the pressure sensor.

15. The method of claim 11, further comprising:
determining a value of the first pressure by providing information to guide the user to touch the pulse wave sensor with the object in a resting state, and determining the value of the first pressure based on whether the AC component of the first pulse wave signal is detected while the object is in contact with the pulse wave sensor in the resting state.

16. The method of claim 11, further comprising:
determining a value of the second pressure by providing information to guide the user to increase the contact pressure to a predetermined pressure or greater, and determining the value of the second pressure based on whether the AC component of the second pulse wave signal is detected at the contact pressure increased to the predetermined pressure or greater.

17. The method of claim 11, wherein the monitoring the vascular health condition comprises, in response to the estimated degree of vasodilation being less than a predetermined threshold, determining an abnormality in a function of a blood vessel.

18. The method of claim 11, further comprising controlling an output interface to output the result of monitoring the vascular health condition.

19. A mobile device for non-invasively monitoring a vascular health condition, the mobile device comprising:
a main body;
a pulse wave sensor mounted in the main body and configured to:
obtain a first pulse wave signal at a first time in a first contact state of an object, wherein the first contact state is a state in which the object touches the pulse wave sensor at a contact pressure of a first pressure and maintains the contact pressure of the first pressure; and
obtain a second pulse wave signal at a second time in a second contact state of the object, wherein the second contact state is a state in which, after the object touches the pulse wave sensor at the contact pressure of the first pressure, gradually increases the contact pressure to a second pressure or higher, and upon satisfaction of a condition, gradually decreases the contact pressure to the first pressure, the object maintains the contact pressure of the first pressure;
a pressure sensor configured to obtain the contact pressure of the object that comes into contact with the pulse wave sensor;
an image sensor configured to capture an image of the object that approaches the pulse wave sensor to obtain the first pulse wave signal and/or the second pulse wave signal;
a display configured to, based on the captured image of the object, display a relative position of the object with respect to a position of the pulse wave sensor; and
a processor mounted in the main body, and configured to:
correct an area of a first alternating current (AC) component of the first pulse wave signal based on a difference, obtained by using the pressure sensor, between a contact pressure of the object at the first time of obtaining the first pulse wave signal and the first pressure corresponding to the first contact state;
correct an area of a second AC component of the second pulse wave signal based on a difference, obtained by using the pressure sensor, between a contact pressure of the object at the second time of obtaining the second pulse wave signal and the second pressure corresponding to the second contact state; and
estimate a first blood volume based on the corrected area of the first AC component, estimate a second blood volume based on the corrected area of the second AC component, estimate a degree of vasodilation based on a difference between the first blood volume and the second blood volume, and output a result of a vascular health condition based on the estimated degree of vasodilation,
wherein the display is configured to output the result of monitoring the vascular health condition,
wherein the processor is further configured to provide information to guide a user to touch the pulse wave sensor with the object at the contact pressure of the first pressure, upon which the first pulse wave signal is obtained, and
wherein the processor is further configured to provide information to guide the user to increase the contact pressure to the second pressure or higher, and upon the satisfaction of the condition, to decrease the contact pressure to the first pressure.

20. The mobile device of claim 19, wherein the processor is further configured to estimate a degree of vasodilation based on an area of an AC component of the first pulse wave signal and an area of an AC component of the second pulse wave signal, and monitor the vascular health condition based on the estimated degree of vasodilation.

21. The mobile device of claim 20, wherein in response to the estimated degree of vasodilation being less than a predetermined threshold, the processor is further configured to determine an abnormality in a function of a blood vessel, and control the display to display a result of determining the abnormality.

22. The mobile device of claim 20, further comprising a communication interface configured to communicate with an external device,
wherein in response to the estimated degree of vasodilation being less than a predetermined threshold, the processor is further configured to determine an abnormality in a function of a blood vessel, and the communication interface is further configured to transmit information related to the vascular health condition to the external device.

* * * * *